United States Patent [19]

Asculai et al.

[11] Patent Number: 4,507,281
[45] Date of Patent: Mar. 26, 1985

[54] INTERFERON-CONTAINING COMPOSITIONS

[75] Inventors: Samuel S. Asculai, East Meadow, N.Y.; Fred Rapp, Hershey, Pa.

[73] Assignee: Exovir, Inc., Great Neck, N.Y.

[21] Appl. No.: 546,573

[22] Filed: Oct. 28, 1983

Related U.S. Application Data

[63] Continuation of Ser. No. 311,035, Oct. 13, 1981, abandoned.

[51] Int. Cl.$^3$ .................. A61K 45/02; C12P 21/00
[52] U.S. Cl. .................. 424/85; 260/112 R; 435/68
[58] Field of Search ............ 424/85, 177; 260/112 R; 435/68

[56] References Cited

U.S. PATENT DOCUMENTS

| | | | |
|---|---|---|---|
| 4,020,183 | 2/1977 | Asculai et al. | 424/341 |
| 4,061,538 | 12/1977 | Dorner et al. | 194/29 |
| 4,139,630 | 2/1979 | Asculai et al. | 424/283 |
| 4,285,929 | 8/1981 | Sugimoto et al. | 424/85 |

FOREIGN PATENT DOCUMENTS 102519  5/1980  Japan .

OTHER PUBLICATIONS

Yancey, K., et al., J. American Academy of Dermatology, pp. 585–595, 1980.
Borzov, M., et al., Vestnik dermatologii i Venerologii, vol. 45, No. 9, pp. 14–17, 1971.
Chemical Abstracts, vol. 94, Abstract No. 185483s, 1981.
Cheeseman, et al., New England Journal of Medicine, vol. 300, pp. 1345–1345, (1979).
Kobza et al., The Lancet, No. 7920, pp. 1343–1344, (1975).
Pazin et al., New England Journal of Medicine, vol. 301, pp. 225–230, (1979).
Scott et al., British Medical Journal, Jun. 28, 1980, pp. 1558–1562.

*Primary Examiner*—Blondel Hazel
*Attorney, Agent, or Firm*—Cooper, Dunham, Clark, Griffin & Moran

[57] ABSTRACT

A composition for treating herpes simplex viral infections in humans is disclosed, comprising about $10^2$ to $10^8$ I.U. of human interferon, about 0.1% to 20% by weight of an antiviral surface active agent, and a physiologically acceptable carrier. Most preferably, the composition comprises about $10^4$ to $10^6$ I.U. of human leukocyte interferon, about 1% to 5% by weight of a nonionic surface active agent having at least one ether or amide linkage, and a physiologically acceptable carrier. A method for treating herpes simplex viral infections in humans is also disclosed, comprising topically administering an effective amount of said antiherpetic composition to the affected area. Most preferably, an effective amount of said antiherpetic composition is topically administered to the affected area during the prodromal stage of viral multiplication.

19 Claims, No Drawings

INTERFERON-CONTAINING COMPOSITIONS

This is a continuation of application Ser. No. 311,035, filed Oct. 13, 1981, now abandoned.

BACKGROUND OF THE INVENTION

This invention relates to a composition and a method for treating herpes simplex infections in humans. More particularly, this invention relates to a pharmaceutical composition containing inferferon and an antiviral surface active agent, and to a method for treating herpes simplex infections in humans by topically administering said pharmeceutical composition to the affected area.

Infections by herpes simplex virus are extremely common in humans. The virus is transmitted by direct contact with infected individuals and it is estimated that more than half the human population has been infected by herpes simplex virus at one time or another.

Once an individual is infected, the virus manifests itself as sores or lesions on various parts of the body. Herpes labialis is the most common clinical form of herpes simplex virus infection. The symptoms include inflammation of the mouth and gums as well as mouth eruptions (cold sores). The cold sores are often painful and unsightly.

In another common clinical form, herpes genitalis, eruptions occur in the genital area. Herpes gentialis is a serious problem. It often causes severe psychological and social problems in affected individuals. It can be fatal to patients with deficient immune systems. In addition, it presents the risk of infections to the newborns of infected mothers, often a fatal disease to the infant.

Herpes simplex virus may also infect the eye producing acute keratitis, and may infect the central nervous system resulting in a severe encephalitis.

Although it was once thought that there was only one type of herpes simplex virus, it is now known that there are two major types of the virus. Herpes simplex virus type 1 (hereinafter HSV-1) is usually associated with herpes labialis. Herpes simplex virus type 2 (hereinafter HSV-2) is usually associated with herpes genitalis. However, HSV-1 has been isolated in some instances from genital lesions, while HSV-2 has been isolated from lesions on parts of the body other than the genitalis. In some reports, HSV-1 has been linked to lip cancer while HSV-2 has been linked to cervical and vulvar cancer.

Following the initial infection with either HSV-1 or HSV-2 lesions may or may not appear. However, the virus does not die but continues to reside in a latent form in the nerve ganglia. Recurrent attacks may occur throughout life in response to non-specific stimuli, for example, in response to changes in body temperature, stress, ultraviolet radiation, hormonal changes, etc. It is believed by some that recurrent attacks occur when the host's immune system is suppressed. At that time, virus latent in the ganglia travels along the nerve cells without damaging them until it emerges from the ends of the nerves. As it emerges, the virus infects the adjacent cells and begins to multiply.

Viral multiplication takes place in two stages eventually resulting in a lesion. In the first stage, known as the prodromal stage, the number of viral particles increases until a first maximum is reached. During this stage, the patient may feel a tingling sensation at the site of viral multiplication. The number of viral particles decreases thereafter. About two to three days after the prodromal stage, the viral particles undergo a second stage of multiplication. In the second stage, the number of viral particles increases until a second maximum, much larger than the first maximum, is reached. The second stage of multiplication causes the death of many cells and results in a lesion. Usually, the lesion heals within 10 to 14 days but in some cases the lesion can last much longer.

Many claims have been made for effective antiherpetic compositions. Undoubtedly, the benefits demonstrated by many of these compositions in in vivo tests may be attributed to a placebo effect. This effect may be as high as 50% for herpes simplex viral infections. One group of chemical agents which proved effective against herpes simplex virus in in vitro tests is the group comprising lipid-dissolving anionic and cationic surface active agents. The effectiveness of these agents has been attributed to their ability to dissolve the lipid-containing membrane which surrounds the nucleocapsid of both HSV-1 and HSV-2.

More recently, it has been discovered by one of the inventors herein along with others that nonionic surface active agents are also effective in reducing the infectivity of herpes simplex virus. For example, in Asculai, S.S., et al., *Antimicrobial Agents and Chemotherapy*, 13, 686 (1978), it is reported that certain nonionic surface active agents rapidly reduced the infectivity of HSV-1 and HSV-2 in vitro. The nonionic surface active agents which inactivated the infectivity of herpes simplex virus were those possessing ether or amide linkages between the hydrophilic and the hydrophobic portions of the molecule. See also U.S. Pat. Nos. 4,020,183 (Asculai, et al.) and 4,139,630 (Asculai, et al.). The therapeutic effect of these nonionic surfactants was also attributed to their ability to dissolve the lipid-containing envelope of herpes simplex virus. The nonionic surfactants were also reported to destroy partially the nucleocapsid of the virus. The nonionic surfactants find use as spermicides in vaginal contraceptives. Contraceptive formulations containing nonionic surfactants were also demonstrated to be effective against herpes simplex virus.

The treatment of herpes simplex virus infections by topical administration of surface active agents, whether anionic, cationic, or nonionic, does not produce entirely satisfactory results. The most beneficial results are obtained when the surfactant is applied during the prodromal stage before the lesion appears. However, it is often difficult to tell when the virus is in the prodromal stage of multiplication. Furthermore, the surface active agent is applied to the uppermost layer of infected cells. Because of the dilution effect, the cells below the uppermost layer do not receive sufficient amounts of the surface active agent to destroy the viral particles. Thus, no protection is provided for cells below the surface layer and herpes simplex virus continues to multiply in those cells below the surface layer. Additionally, treatment with the antiviral surface active agent does not appear to reduce the frequency of recurrent attacks. It is believed however, that recurrent attacks might be prevented if sufficient numbers of the multiplying viral particles are destroyed.

It would thus be desirable to provide a pharmaceutical composition which reduces the load of herpes simplex virus so that latency is not reestablished.

It would also be desirable to provide a pharmaceutical composition which prevents spread of the virus to cells below the surface layer.

Human interferon is known to protect cells against viral infections. Human interferon is produced by cells in reaction to the presence of specific inducers, such as viruses. It may be produced in vivo by the cells of living organisms, or it may be produced in vitro by cell cultures in response to the presence of the inducer. There are now known to be three main varieties of human interferon: leukocyte or α, fibroblast or β, and immune or γ interferon. There are also known to be several sub-varieties of human leukocyte and fibroblast interferon.

Human interferon is relatively nontoxic and nonantigenic in humans. It is also extremely effective against a broad spectrum of viruses, including herpes simplex virus, even at very low concentrations. Until the present, treatment of herpetic lesions with human interferon has proceeded along two main courses: (a) medicinal induction of endogenic interferon in the patient, and (b) administration of exogenic interferon to the patient.

For example, U.S. Pat. No. 4,053,582 (Stickl) discloses a method for treating herpes simplex infections in humans by administering attenuated fowl pox virus to the patient. The attenuated virus induces the patient to produce his own interferon. The herpetic lesions heal within a short time after induction.

U.S. Pat. Nos. 4,061,538 (Dorner et al.) and 4,184,917 (Dorner et al.) disclose a method of treating herpes simplex viral infections by administering structurally modified interferons to the patient. In these patients, the modified interferons are administered systemically to the patient.

Several published reports also disclose the treatment of herpetic eye infections by topical administration of human interferon. For example, see D. Naumann-Haefelin, et al., in *Infection and Immunity*, 17, 468 (1977) and B. R. Jones, et al., in *Lancet ii*, 128 (1976).

None of these disclosures suggests the treatment of herpes labialis and herpes genitalis in humans by administering topically an interferon-containing pharmaceutical composition. Moreover, none of these disclosures suggests the treatment of herpes simplex viral infections by administering topically a combination of human interferon and an antiviral surface active agent.

Accordingly, it is an object of the present invention to provide novel pharmaceutical compositions containing human interferon and an antiviral surface active agent.

It is also an object of the present invention to provide a method for treating lesions due to herpes simplex virus by topically administering the aforesaid pharmaceutical compositions.

It is further an object of the present invention to provide compositions for treating herpetic lesions which not only heal the lesions but may also reduce recurrent attacks.

How these and other objects of this invention are achieved will become apparent in light of the accompanying disclosure and claims.

SUMMARY OF THE INVENTION

A composition for treating herpes simplex viral infections comprises about $10^2$ to $10^8$ I.U. of human interferon, about 0.1% to 20% by weight of an antiviral surface active agent, and a physiologically acceptable carrier. Most preferably, a composition for treating herpes simplex viral infections comprises about $10^4$ to $10^6$ I.U. human leukocyte interferon, about 1% to 5% by weight of a nonionic surface active agent having at least one ether or amide linkage, and a physiologically acceptable carrier.

A method for treating herpes simplex viral infections in humans comprises topically administering to the affected area an effective amount of said compositions. Most preferably, a method for treating herpes simplex viral infections in humans comprises topically administering to the affected area an effective amount of said compositions during the prodromal stage of viral multiplication.

DETAILED DESCRIPTION OF THE INVENTION

The novel pharmaceutical compositions of the present invention contain effective amounts of human interferon, an antiviral surface active agent, and a physiologically acceptable carrier. The pharmaceutical compositions may contain any of the known varieties or sub-varieties of human interferon. Thus, the composition may contain human leukocyte, fibroblast, or immune interferon. Additionally, the interferon may suitably be prepared by "classical" culture methods or by recombinant DNA methods. An effective dosage of human interferon for treating herpetic lesions in accordance with the practices of the present invention is about $10^2$ to $10^8$, preferably about $10^4$ to $10^6$, I.U.

The antiviral surface active agent may be anionic, cationic, or, preferably, nonionic. Antiviral surface active agents are known in the art. These surfactants dramatically reduce the infectivity of HSV-1 and HSV-2 by damaging or destroying the lipid envelope of the virus. Suitable anionic surfactants include sodium alkylsulfonates and sodium alkylbenzenesulfonates. Suitable cationic surfactants include quaternary ammonium detergents, such as cetyl pyridinium chloride, and benzalkonium chlorides.

Nonionic surface active agents are preferred in the pharmaceutical preparations of the present invention. In contrast to cationic, anionic, and ampholytic surface active agents, the nonionics contain no ionizable groups and have no surface charge. They depend upon their entire molecule for surface activity. Almost any hydrophobic compound which has in its structure a carboxy, hydroxy, amido or amino group with a free hydrogen attached to the nitrogen, can be reacted with ethylene oxide to form a nonionic surfactant. At least three groups of nonionic surfactants are recognized: (a) those having an ether linkage between the hydrophilic and hydrophobic portions of the molecule, (b) those having an ester or ether-ester linkage, and (c) those having an amide linkage. Nonionic surfactants having at least one ether or amide linkage are preferred for purposes of the present invention. Examples of preferred nonionic surfactants include the following: nonylphenoxypolyethoxy ethanol (available under the trade name Nonoxynol-9), p-diisobutylphenoxypolyethoxy ethanol (available under the trade name Triton X-100), polyoxyethylene (10) oleyl ether (available under the trade name Brij-97), and onyx-ol (available under the trade name Onyx-ol 345).

An effective dosage of an antiviral surface active agent for purposes of the present inventions comprises about 0.1% to 20% by weight of the pharmaceutical composition. The preferred range is about 1% to 5% by weight.

The balance of the pharmaceutical compositions comprises an inert, physiologically acceptable carrier. The carrier should not react with the active ingredients and not reduce their effectiveness. Suitable physiologically acceptable carriers include water, ethanol, polyethylene glycol, mineral oil, petrolatum, propylene glycol, and the like. The pharmaceutical compositions are preferably administered in lotion, cream, oil, or emulsion formulations.

The following are examples of suitable formulations containing a nonionic surfactant and human interferon:

| Pharmaceutical Lotion | |
|---|---|
| propylene glycol | 24.75 ml. |
| triethanolamine | 1.00 ml. |
| water | 7.00 ml. |
| oleic acid | 1.50 gm. |
| polyethylene glycol monostearate | 10.50 gm. |
| silicon fluids | 10.00 ml. |
| carbopol-934 (2% mucilage) | 50.00 ml. |
| human leukocyte interferon | $10^6$–$10^8$ I.U. |
| Pharmaceutical Cream A | |
| white petrolatum | 41.00 gm. |
| microcrystalline wax | 3.00 gm. |
| fluid lanolin | 10.00 gm. |
| sorbitan monooleate | 4.75 gm. |
| polysorbate-80 | 0.25 gm. |
| purified water | 41.00 gm. |
| human leukocyte interferon | $10^6$–$10^8$ I.U. |
| Pharmaceutical Cream B | |
| spermaceti | 7.5% |
| white wax | 12.0% |
| mineral oil | 56.0% |
| sodium borate | 0.5% |
| sorbitan monooleate | 5.0% |
| water | 19.0% |
| human leukocyte interferon | $10^5$–$10^7$ I.U. |

Topical administration of pharmaceutical compositions of the present invention may be effected by applying a small amount (e.g., about 1 ml) of the compositions directly to and in areas adjacent to the site of the lesions with a cotton swab, soft brush, sponge or the like. Any quantity sufficient to cover the area of the lesions is effective. Treatment with the pharmaceutical compositions herein disclosed should be frequent, for example, every 2-4 hours, for about 3-4 days. Preferably, the pharmaceutical compositions are applied during an early stage of viral multiplication. For example, the compositions may be applied during the prodromal stage in the areas where a tingling sensation is felt. When the compositions are applied to lesions, the pain is substantially reduced within 1 hour in almost all cases. The lesions are noticeably improved within 4 to 12 hours, and are completely healed within 4 to 5 days with little or no scarring. When the compositions are applied during the prodromal stage, the tingling sensation usually disappears within the hour and the compositions provide a prophylaxis against emergence of the lesions. In some cases, no lesion appears at all; in other cases, a small blister appears which disappears within 2-3 days. Additionally, treatment of herpes simplex virus infections in accordance with the present invention appears to reduce the frequency of recurrent attacks and in some cases apparently eliminates the virus altogether. No contraindications have been found.

The pharmaceutical compositions of the present invention also display antimicrobial activity as well as antiviral activity. For example, they are effective in treating warts as well as bacterial infections. As used herein, the term antimicrobial activity refers to activity against microorganisms other than viruses such as bacteria and fungi.

In addition to direct application, the pharmaceutical compositions may be administered topically by various other methods. For example, the compositions may be delivered to the affected region in microencapsulated form. They may also be delivered in a foam, by spray, tampon, vaginal suppository, etc.

Although it is not completely understood, it is believed that the pharmaceutical compositions herein disclosed operate in the following manner. The antiviral surface active agent dissolves the lipid-containing envelopes of herpes simplex virus thereby destroying its infectivity. The interferon aids the cells in preventing viral replication. In addition, because very few interferon molecules are needed to protect a cell, the interferon prevents the spread of the virus to cells below the uppermost layer. Thus, the combination of a surface active agent, such as a nonionic surface active agent, and human interferon is more effective against herpes simplex virus than would be expected by simply adding the effectiveness of the two active ingredients. It is believed that this synergistic effect retards recurrent attacks of the virus.

In another embodiment, this invention comprises a cosmetic composition containing effective amounts of human interferon, an antiviral surface active agent, and a physiologically acceptable cosmetic carrier. Additional components, for example, skin softeners, may be included in the cosmetic formulations.

Cosmetic formulations are known in the art and are usually hypoallergenic and pH controlled. The cosmetic formulations of this invention are used as a prophylactic to prevent outbreak of herpetic lesions. They may be applied nightly. Cosmetic formulations according to the present invention generally contain less human interferon and antiviral surface active agent than pharmaceutical preparations. The preferred range of human interferon is $10^3$–$10^5$ I.U. and the preferred range of the antiviral surface active agent is 0.1%–1%. A nonionic antiviral surface active agent is preferred. A typical cosmetic formulation according to the present invention is the following:

| Cosmetic Cream | |
|---|---|
| beeswax | 12.1% |
| spermaceti | 12.6% |
| sweet almond oil | 54.4% |
| borax | 0.5% |
| rose water | 19.4% |
| onyxol | 1.0% |
| human leukocyte interferon | $10^3$–$10^5$ I.U. |

The following examples are presented in further illustration of the practices of the present invention.

EXAMPLE 1

To determine whether human interferon is compatible with antiviral surface active agents, monolayers of human embryo cells were grown. Human leukocyte interferon ($10^5$ I.U.) was mixed with a 1% solution of nonylphenoxypolyethoxyethanol (without a carrier) and with a proprietary cream formulation containing 1% nonylphenoxypolyethoxyethanol (Stearox). The interferon was kept in contact with the nonionic antiviral surfactant overnight and the mixture was then diluted 1:$10^4$ with a standard medium saline solution. The mixture was then applied to the monolayers of human embryo cells overnight at 37%C. The next day the human embryo cells were exposed to vesicular stomatitis virus and after a suitable period of time the cultures were assayed for virus plaques. The assays were compared to assays taken when the cells were exposed to vesicular stomatitis virus without the benefit of any antiviral agent and with the benefit of human leukocyte interferon alone (diluted as above). The results demonstrate that there is no reduction in activity of human interferon when combined with the nonionic surface active agent.

EXAMPLE 2

The procedure of Example 1 was followed except that the human embryo cells were exposed to herpes simplex virus types 1 and 2 instead of vesicular stomatitis virus. The results demonstrate that human interferon remains active against herpes simplex virus in the presence of an antiviral surface active agent. The tests show that human interferon is compatible with an antiviral surface active agent.

EXAMPLE 3

Patient A, a female, suffers recurrent herpes simplex virus infections of the face. Lesions erupt approximately every 3 to 4 months and cover most of her face. The next time she feels a tingling sensation indicating the prodromal stage of viral multiplication, she applies the pharmaceutical lotion described above directly to her entire face. The lotion is applied every 2 hours while she is awake for 3 days. The tingling sensation disappears within an hour after the first application. Two days after the first application, a small blister appears on her lip. The blister disappears a day later leaving no scar. Patient does not report any subsequent outbreaks.

EXAMPLE 4

Patient B, a female, suffers from recurrent attacks of herpes genitalis. On the average, outbreaks occur every 8 weeks and symptoms last for about 2 weeks. She is treated with the pharmaceutical cream A described above during the prodromal stage of her next outbreak. The cream is applied every 4 hours for 3 days. The tingling sensation disappears almost immediately and no eruptions are subsequently observed. Recurrent outbreaks are also not reported.

EXAMPLE 5

Patient C, a male, suffers from recurrent attacks of herpes genitalis. Eruptions appear every 3–4 months on the average and last about 10–14 days. At the next outbreak, a pharmeceutical cream B described above is applied as soon as the eruptions begin to appear. The pharmaceutical cream is applied every 2 hours. The eruptions are much smaller and fewer in number than usually appear and last for only 2 days. Patient C thereafter applies the cosmetic cream described above once a day. No subsequent outbreaks are reported.

While the invention has been described by reference to specific embodiments, this was for purpose of illustration only and should not be construed to limit the spirit or the scope of the invention.

We claim:

1. A therapeutic composition for treating herpes simplex viral infections in humans, comprising an effective amount of human interferon, an effective amount of nonylphenoxypolyethoxyethanol, and a physiologically acceptable carrier.

2. A composition as in claim 1, wherein the amount of human interferon is from about $10^2$ to $10^8$ I.U.

3. A composition as in claim 1, wherein the amount of human interferon is from about $10^4$ to $10^6$ I.U.

4. A composition as in claim 1, wherein the amount of nonylphenoxypolyethoxyethanol is from about 0.1% to 20% by weight of said composition.

5. A composition as in claim 1, wherein the amount of nonylphenoxypolyethoxyethanol is from about 1% to 5% by weight of said composition.

6. A composition as in claim 1, wherein the human interferon is leukocyte interferon.

7. A composition as in claim 1, wherein the carrier comprises water, ethanol, polyethylene glycol, mineral oil, petrolatum, or propylene glycol.

8. A composition as in claim 1, wherein said carrier is a pharmaceutically acceptable carrier.

9. A composition as in claim 1, wherein said carrier is a cosmetically acceptable carrier.

10. A method for treating herpes simplex viral infections in humans, comprising topically administering to an affected area an effective amount of a therapeutic composition comprising human interferon, nonylphenoxypolyethoxyethanol, and a physiologically acceptable carrier.

11. A method as in claim 10, wherein the amount of human interferon is from about $10^2$ to $10^8$ I.U.

12. A method as in claim 10, wherein the amount of human interferon is from about $10^4$ to $10^6$ I.U.

13. A method as in claim 10, wherein the amount of nonylphenoxypolyethoxyethanol is from about 0.1% to 20% by weight of said composition.

14. A method as in claim 10, wherein the amount of nonylphenoxypolyethoxyethanol is from about 1% to 5% by weight of said composition.

15. A method as in claim 10, wherein said human interferon is human leukocyte interferon.

16. A method as in claim 10, wherein said therapeutic composition is topically administered to an affected area prior to the appearance of a lesion due to herpes simplex viral infection.

17. A method as in claim 10, wherein said therapeutic composition is applied to the genital area of a human.

18. A method as in claim 10, wherein said composition is applied in a foam, spray, tampon or vaginal suppository.

19. A method as in claim 10, wherein said composition is applied about every 2–4 hours.

* * * * *